United States Patent [19]

Besnier et al.

[11] Patent Number: 5,776,418
[45] Date of Patent: Jul. 7, 1998

[54] AUTOMATED ANALYSIS APPARATUS HAVING FIXED CELLS

[75] Inventors: Joseph Besnier, Sonnobeaunout-Hague; Gilbert Ringot, Querqueviue, both of France

[73] Assignee: Compagnie Generale Des Matieres Nucleaires, Velizy Villacoublay, France

[21] Appl. No.: 705,920

[22] Filed: Aug. 29, 1996

Related U.S. Application Data

[63] Continuation of Ser. No. 393,163, Feb. 21, 1995, abandoned.

[30] Foreign Application Priority Data

Feb. 23, 1994 [FR] France .................................. 94 02045

[51] Int. Cl.$^6$ .................................................. G01N 33/00
[52] U.S. Cl. .......................... 422/68.1; 422/63; 422/67; 422/75; 422/81; 422/100; 436/52; 436/163; 436/180; 73/863.1; 73/863.73; 141/130
[58] Field of Search .................... 422/67, 63, 68.1, 422/75, 81, 100, 103; 436/52, 163, 180; 73/863.1, 863.71, 863.72, 863.73; 141/51, 97, 130

[56] References Cited

U.S. PATENT DOCUMENTS

| | | | |
|---|---|---|---|
| 4,231,862 | 11/1980 | Mona et al. | 210/601 |
| 4,266,950 | 5/1981 | Makino et al. | 55/196 |
| 4,359,447 | 11/1982 | Welch | 422/63 |
| 4,662,231 | 5/1987 | Schaarschmidt | 73/863 |
| 4,708,940 | 11/1987 | Yoshida et al. | 436/45 |
| 4,792,434 | 12/1988 | Metzger et al. | 422/100 |
| 4,832,914 | 5/1989 | Tam et al. | 422/130 |
| 4,854,355 | 8/1989 | Chazot et al. | 141/130 |
| 4,925,628 | 5/1990 | Metzger et al. | 422/100 |
| 4,980,130 | 12/1990 | Metzger et al. | 422/70 |
| 4,999,305 | 3/1991 | Wolcott et al. | 436/52 |
| 5,012,845 | 5/1991 | Averett | 141/329 |
| 5,181,419 | 1/1993 | Thompson | 73/153 |
| 5,247,972 | 9/1993 | Tetreault | 144/27 |
| 5,328,662 | 7/1994 | Ringot et al. | 422/63 |

FOREIGN PATENT DOCUMENTS

| | | |
|---|---|---|
| 0286536 | 10/1988 | European Pat. Off. . |
| 0532404 | 3/1993 | European Pat. Off. . |

OTHER PUBLICATIONS

Review of Scientific Instruments, USA, vol. 59, No. 12, pp. 2609–2615—Dec. 1988, ISSN 0034-6748—Sweileh J. A. et al., "Novel Automated Micro Batch Analyzer".

*Primary Examiner*—Harold Y. Pyon
*Attorney, Agent, or Firm*—Pearne, Gordon, McCoy and Granger LLP

[57] ABSTRACT

An apparatus is proposed making it possible in automated manner to perform several analyses on the same sample. For this purpose several fixed, chemical preparation cells (10) can separately receive several fractions of the same sample. Reagent injection systems (24) associated with these cells, as well as stirrers (14) make it possible to prepare, in each of them, a chemical preparation which is transferred into an analysis cell (36) associated therewith by an air ejector (44). The same ejector discharges the preparation to the drain (38) when the analysis has been completed. Ducts (70, 72), as well as a discharge line (62) then make it possible to wash, rinse and empty each chemical preparation cell (10).

11 Claims, 5 Drawing Sheets

AUTOMATED ANALYSIS APPARATUS HAVING FIXED CELLS

This is a continuation of application Ser. No. 08/393,163, filed Feb. 21, 1995 now abandoned.

BACKGROUND OF THE INVENTION

The present invention relates to an analysis apparatus designed for the carrying out in an automated manner of a number of analyses on the same liquid sample.

The invention applies advantageously, but not exclusively to the performance of several chemical analyses on liquid samples taken at different points of a production or treatment line for products such as radioactive products.

Within the scope of the latter application, the analysis apparatus according to the invention can be more particularly used in an automated installation like that described in FR-A-2 675 582. In said installation, liquid products are sampled in automated manner at different points of a production or processing line and are introduced into tight jugs. The latter are then automatically transferred into analysis containers by pneumatic transfer circuits.

Although the installation described in FR-A-2 675 582 permits the automatic sampling of samples and their transfer into analysis containers, the operations which are then performed within the latter take place manually with the aid of grippers. Thus, the jugs which have dropped in bulk into the bottom of the analysis containers must then be identified by reading a code and opened with the aid of a gripper. Sampling operations are then carried out in the open jug by means of a laboratory pipette. Finally, all the operations necessary for carrying out the desired analyses (the addition of reagents, transfers, etc.) are performed manually, with the aid of grippers and using conventional laboratory equipment such as syringes, glassware, etc.

When they are applied to the monitoring of an industrial production or processing line, these operations are inappropriate and give rise to a non-negligible risk of error. Moreover, they are tedious, expensive and lead to an increase in the amount of solid waste and liquid effluents, more particularly due to the fact that only one analysis can take place on one sample.

Moreover, the automation of the chemical analyses performed in the aforementioned analysis containers is unable to take account of a certain number of factors. A first of these factors concerns the wish to be able to progressively equip existing analysis containers with automated analysis apparatuses without it being necessary to completely replace the containers.

Moreover, when it is a question of analyzing radioactive products, the design of such an analysis apparatus must take account of the constraints imposed by such products. Thus, the technologies used must be reliable and permit maintenance with the aid of handling grippers equipping the container. In addition, radiological protection must be ensured taking account both of irradiation and contamination. To take account of the latter, the extent of the displacements must be limited so as to prevent the progression in time of the contamination towards the exterior of the analysis containers.

Although, it is not excluded in certain cases that only a single analysis may be needed on the same sample, it is desirable with a view to reducing the quantity of solid waste and liquid effluents, to be able to simultaneously perform several analyses on a single sample contained in the same jug. In order not to make the system excessively complex, this requires making the analysis apparatus completely independent of the automated systems which may be placed upstream of said apparatus within the analysis containers, particularly for opening the jugs and taking the samples. These upstream systems, which do not form part of the present invention, can in particular be controlled by a process controller, whereas the putting into operation of the analysis apparatus according to the invention and which requires the taking into account of analog values, clock rates, delays, volumes, potentials, etc. requires the use of a microprocessor.

The invention more specifically relates to an automated analysis apparatus which in particular, but not exclusively can be used in an automated installation like that described in FR-A-2 675 582, e.g. in association with a device making it possible to open the jugs and take liquid samples therefrom, so as to permit a complete automation of the analyses reducing to a minimum value the solid waste and liquid effluents, whilst significantly improving productivity.

SUMMARY OF THE INVENTION

According to the invention this result is achieved by means of an automated analysis apparatus, which comprises:

at least two analysis lines, each including:
  a fixed chemical preparation cell,
  a means for stirring a liquid placed in the cell,
  means for injecting reagents into the cell,
  an analysis cell equipped with analysis means,
  a line for transferring liquid placed in the preparation cell into the analysis cell and then from the latter to an effluent discharge system,
  a discharge line directly linking the chemical preparation cell to the effluent discharge system, distributing means for introducing a liquid sample to be analyzed into at least one of the chemical preparation cells and control means controlling at least the stirring means, the injection means, the analysis means, the transfer line and the discharge line.

The use of such an apparatus makes it possible to simultaneously and in automated manner perform several analyses on the same liquid sample. Apart from the automation of the analyses, the simultaneous nature thereof leads to a considerable time gain, because the total duration of the analyses does not exceed the duration of the longest analysis.

Moreover, the automation of the analyses makes it possible to reduce the liquid effluents to a minimum value by limiting the quantities of samples used, as well as the quantities of reagents to minimum values. The quantity of solid waste is also reduced by the fact that when the liquid product to be analyzed is initially contained in a jug, a sample taken therefrom can be used for making several analyses, so that there is a reduction in the number of jugs.

In a preferred embodiment of the invention, the chemical preparation cells are placed in a tight enclosure. The reagent injection means then comprise at least one injection apparatus positioned outside the enclosure and at least one catheter connecting said injection apparatus to the chemical preparation cell. This catheter then passes through a roof or top flange of the enclosure and is placed, below said flange, in a vertical guide tube.

In this preferred embodiment of the invention, each transfer line comprises a first tube connecting the chemical preparation cell to the analysis cell, a second tube connecting the analysis cell to a first air ejector common to all the analysis lines and connected to the effluent discharge system and a valve placed in the second tube upstream of the air ejector.

In order that the liquid quantity admitted into the analysis cell is perfectly controlled, the air ejector advantageously has a programmed delay, constant pressure, motorized air supply.

In the preferred embodiment of the invention, the discharge line incorporates a third tube connecting the chemical preparation cell to a second air ejector common to all the analysis lines and connected to the effluent discharge system, as well as a second valve placed in the third tube upstream of the second ejector.

Each of the valves placed in the second and third tubes is constituted either by an electrovalve, or by a pneumatic control valve actuated by a control electrovalve located outside the enclosure.

To permit the rinsing and drying of the chemical preparation cell of each analysis line, said line preferably also has a pipe for supplying a rinsing product into the chemical preparation cell and a drying pipe for said cell.

In order to facilitate maintenance operations, the chemical preparation cells of all the analysis lines can be installed on the same retractable plate, which is vertically movable between an upper working position and a lower maintenance position.

As a variant, each chemical preparation cell can be placed on an individual support, which can be installed, with the aid of a handling gripper and by acting on an articulated fixing collar, on the vertical guide tube associated with the cell in question.

The distributing means used for supplying the chemical preparation cells can then have a vertical suction fitting mounted on positioning means, so as to be positionable at random, by an actuation of said positioning means, above a container such as a jug containing the liquid to be analyzed or above any random one of the chemical preparation cells.

As a function of the nature of the analyses to be performed, each of the analysis lines can also incorporate one or more measuring or control apparatuses placed in the chemical preparation cell and connected to instrumentation located outside the enclosure by a vertical cable passing through the top flange of the enclosure.

BRIEF DESCRIPTION OF THE DRAWINGS

The invention is described in greater detail hereinafter relative to two non-limitative, but preferred embodiments and with reference to the attached drawings, wherein show.

DETAILED DESCRIPTION OF PREFERRED EMBODIMENTS

Figure 1:
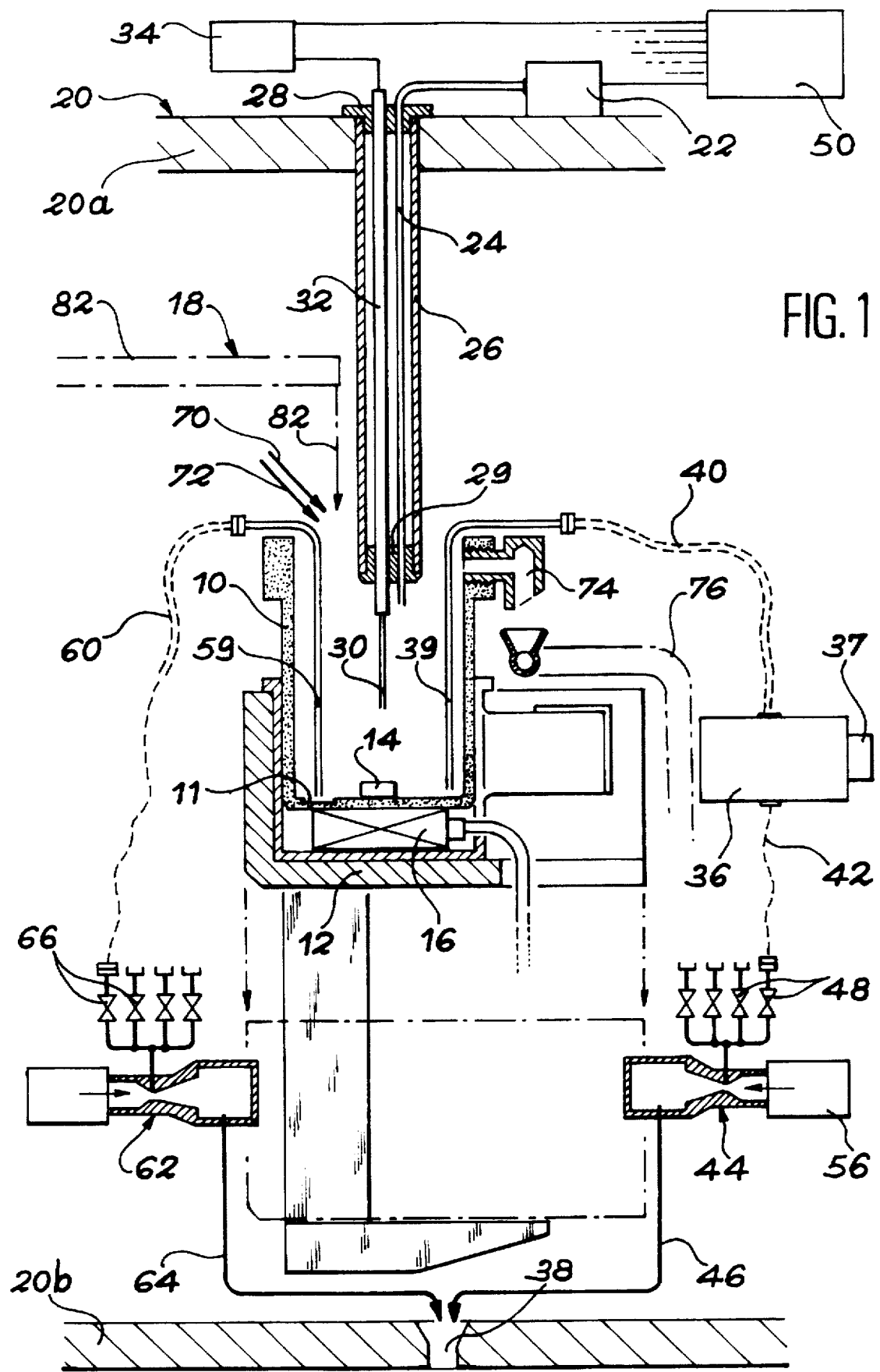
FIG. 1 A side view in partial section diagrammatically illustrating one of the analysis lines of an automated analysis apparatus according to a first embodiment of the invention.

As will become more readily apparent hereinafter, the automated analysis apparatus according to the invention has at least two analysis lines on which can be automatically performed in simultaneous manner a number of analyses on the same liquid sample. All these analysis lines are produced according to the same principle, which will now be described relative to FIG. 1.

Each of the analysis lines of the automated analysis apparatus according to the invention firstly has a fixed, chemical preparation cell 10. In the embodiment illustrated in FIGS. 1 to 5, the cells 10 of all the analysis lines are installed on the same horizontal support plate 12 in accordance with a layout to be defined hereinafter.

A stirrer 14 is placed in each of the chemical preparation cells 10. The stirrer is operated by an e.g. magnetic or ultrasonic motor 16 placed beneath the bottom of the cell. The motor 16 is installed in the horizontal support plate 12.

Distributing means 18, to be described in greater detail hereinafter, make it possible to introduce a sample to be analyzed into one or more chemical preparation cells 10. It should be noted that the distributing means 18 are common to all the analysis lines of the apparatus and are controlled independently of said lines, e.g. by a process controller.

In the embodiments illustrated in the drawings, which relate to the case where the liquid samples to be analyzed are radioactive, the chemical preparation cells 10 as well as their support plate 12 and the distributing means 18 are placed in tight enclosure 20, whose roof flange and a bottom are respectively illustrated at 20a and 20b in FIG. 1.

Each of the analysis lines of the automated analysis apparatus according to the invention also has injection means permitting the introduction into the chemical preparation cell 10 of one or more reagents necessary for the envisaged analysis, as well as the water optionally needed for diluting the products admitted into the cell. These reagent injection means comprise injectors 22 positioned outside the enclosure, e.g. above the top flange 20a. Each of these injectors 22 makes it possible to introduce into the chemical preparation cell 10 in question a given reagent quantity by means of a catheter 24 formed by a polytetrafluoroethylene microtube. This catheter 24 passes through the top flange 20a vertically of the considered chemical preparation cell 10 and descends vertically into the cell within a guide tube 26. More specifically, all the catheters 24 associated with the same chemical preparation cell 10 are placed in the same guide tube 26. The guide tube 26 can in particular be made from stainless steel. Plugs 28, 29 traversing the catheter or catheters 24 tightly seal the guide tube 26, respectively at its upper and lower ends.

Measuring or control apparatuses such as a conductometry or temperature probe can be placed, if necessary, in the chemical preparation cell 10 of certain analysis lines. Such an apparatus 30 is diagrammatically illustrated in FIG. 1 below the plug 29 sealing the guide tube 26 at its lower end. It will be shown hereinafter with reference to FIGS. 4 and 5 that a different arrangement can be adopted in practice. As a function of the nature of the apparatus 30, an optical, electrical or similar connection cable 32 connects the apparatus 30 to a supply and measuring system 34 located outside the enclosure 20.

Each of the analysis lines of the automated analysis apparatus according to the invention also has an analysis cell 36 for receiving a clearly defined quantity of the chemical preparation prepared in the cell 10, in order to perform an analysis of the sample in question with the aid of an analysis apparatus 37 equipping said analysis cell 36. This analysis apparatus 37 can in particular be a spectrophotometer or a chromatograph. As a function of the particular case, the analysis cell 36 is installed inside or outside the enclosure 20. The embodiment illustrated in FIG. 1 corresponds to the installation of said cell 36 within the enclosure.

A transfer line connects each of the chemical preparation cells 10 to the corresponding analysis cell 36 and connects the latter to an effluent discharge system represented in FIG. 1 by a siphon 38 in the bottom 20b of the enclosure.

More specifically, said transfer line has a rigid tube 39 immersed in the chemical preparation cell 10 up to the vicinity of its bottom and a first flexible tube 40 connecting the rigid tube 39 to the analysis cell 36. The transfer line also has a second flexible tube 42 connecting the analysis cell 36 to the inlet of an air ejector 44. The outlet of the air ejector 44 is connected to the siphon 38 by a rigid tube 46.

The automated analysis apparatus illustrated by the drawings has a single air ejector 44 common to all the analysis lines. Consequently the inlet of said air ejector 44 is connected to each of the analysis cells 36 by a tube 42 incorporating a valve 48.

In the embodiment illustrated in FIG. 1, the valves 48 are pneumatic control valves controlled by not shown, control electrovalves located outside the enclosure 20. These control electrovalves are placed on control pipes connecting each of the valves 48 to a compressed air source.

In a not shown variant, the valves 48 are preferably low voltage electrovalves. These electrovalves can in particular be embedded in a protective resin, so that they are completely insulated from the possibly corrosive atmosphere contained in the enclosure. Compared with the embodiment of FIG. 1, this variant makes it possible to use commercially available valves and to simplify the system by dividing the number of valves by two. Moreover, when the atmosphere is corrosive, the anticorrosion protection provided by the resin is total, which is not the case with pneumatic control valves, which necessarily have an air discharge orifice.

The air ejector 44 is controlled by the compressed air admitted by a not shown pipe through a controlled, timed flow rate control system 56.

Each of the analysis lines of the automated analysis apparatus illustrated in FIG. 1 also has a discharge line making it possible to discharge the products present in the chemical preparation cell 10 directly to the effluent discharge system represented by the siphon 38, when the analysis is completed.

In the embodiment illustrated in FIG. 1, said discharge line has a rigid tube 59, which is immersed in the bottom of the chemical preparation cell 10 and a flexible tube 60 connecting the rigid tube 59 to a second air ejector 62. So as to permit the complete draining of the chemical preparation cell 10, the latter advantageously has a not shown, slightly inclined bottom, whose bottom point forms a recovery chute or channel 11 and the lower end of the rigid tube 59 is immersed in the bottom of said channel 11. The outlet of the air ejector 62 is connected by a rigid tube 64 to the siphon 38.

In the same way as the air ejector 44, the air ejector 62 is a single ejector common to all the analysis lines. Consequently each of the flexible tubes 60 is connected to said air ejector 62 by means of a valve 66. Like the valves 48, the valves 66 can either be electrovalves, or pneumatic control valves controlled by not shown electrovalves placed in pipes connecting each of the valves 66 to a compressed air source. The air ejector 62 is controlled by the compressed air admitted by a not shown pipe.

Apart from the draining or emptying of the chemical preparation cell 10, the discharge line described hereinbefore also participates in the rinsing of said cell, together with a rinsing duct 70, which also issues above each of the chemical preparation cells 10. This rinsing duct 70 can be used for introducing into the cell 10 both rinsing water and some other rinsing product such as alcohol able to rapidly dry when the air is injected into the cell 10 by a drying duct 72.

It should finally be noted that the chemical preparation cell 10 is advantageously equipped with an overflow system 74 directly connected to the siphon 38 by a pipe 76.

As is very diagrammatically shown in FIG. 1, control means such as a microprocessor 50 are provided outside the enclosure 20 for controlling all the functions of the analysis apparatus according to the invention, with the exception of the distributing means 18. Thus, the microprocessor 50 controls the motor 16 of the stirrers 14, the reagent and water injectors 22, 34, the rinsing and drying systems associated with the ducts 70, 72, the transfer and discharge lines of the chemical preparation cells 10 and the analysis apparatuses 37.

A practical embodiment of an automated analysis apparatus having four analysis lines in accordance with the first embodiment described hereinbefore relative to FIG. 1 will now be described with reference to FIGS. 2 to 5.

Figure 2:
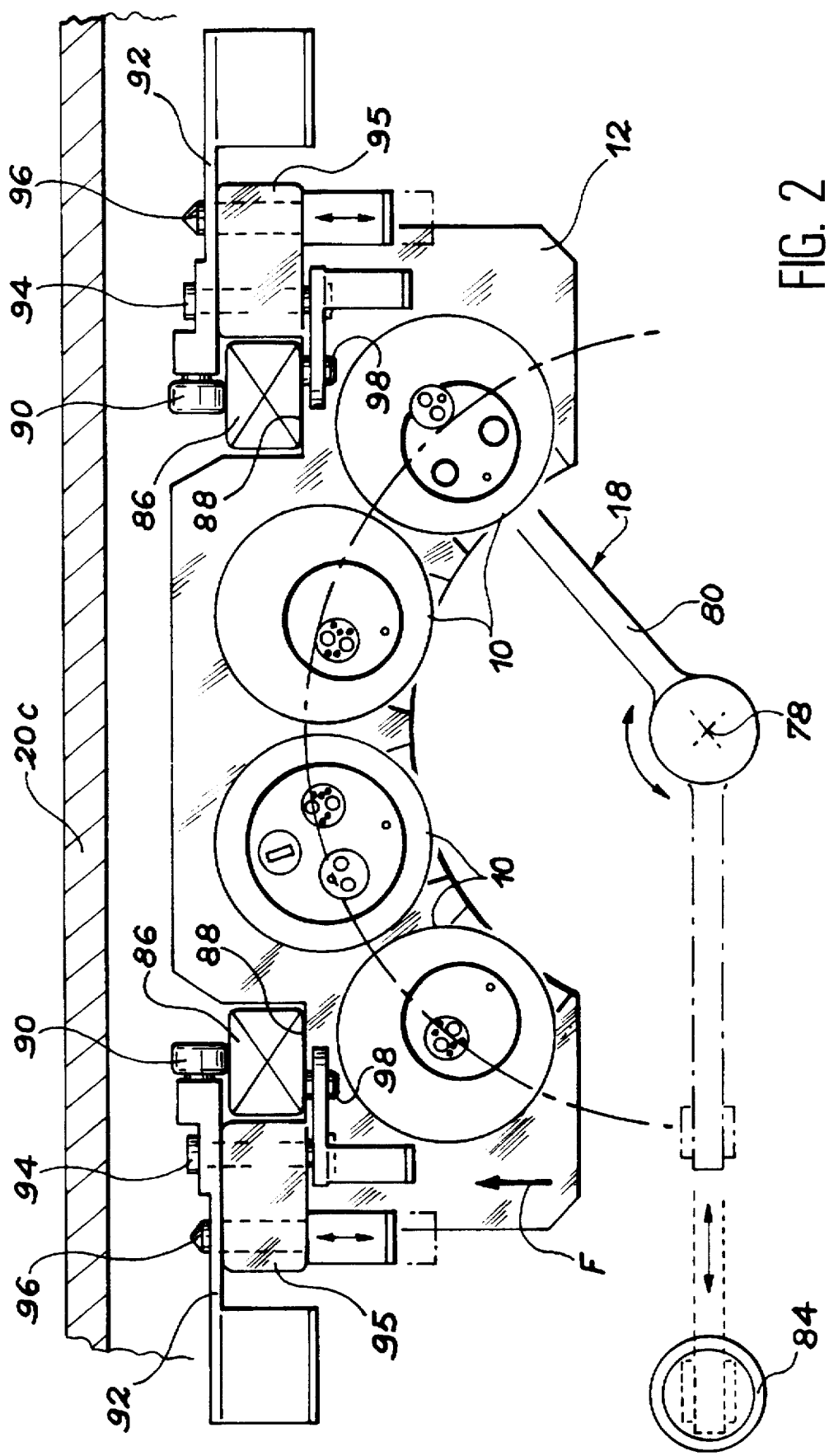
FIG. 2 A plan view illustrating in greater detail an embodiment of the automated analysis apparatus of FIG. 1.

On firstly referring to FIG. 2, it can be seen that in this embodiment of the invention the horizontal support plate 12 carries four chemical preparation cells 10. These cells 10 are identical having in section a circular shape, the centers of the circles being equidistant of one another on a circular arc centred on a vertical axis 78. This vertical axis 78 serves as the rotation axis for a horizontal and optionally telescopic arm 80 belonging to the distributing means 18 in FIG. 1.

At its end opposite to the axis 78, the horizontal arm 80 has a suction fitting 82 (FIG. 1) which can be placed above any random one of the chemical preparation cells 10 and above a jug 84 containing the liquid to be analyzed during the rotation of the arm 80 around the axis 78.

If the jug 84 is not on the same circular axis as the chemical preparation cells 10, in the manner illustrated in FIG. 2, the arm 80 is telescopic. Moreover, it performs a rise and fall movement authorizing, in the upper position, its displacement above the cells 10 and the jug 84 and in the lower position the suction of the liquid contained in the jug by the suction fitting 82. The different motors controlling the aforementioned movements of the arm 80 are advantageously positioned outside the enclosure and in particular above the top flange 20a. They are controlled by a not shown process controller independently of the apparatuses constituting the automated analysis apparatus according to the invention.

The horizontal support plate 12 carrying the chemical preparation cells 10 occupies a fixed position within the enclosure when the automated analysis apparatus is in operation. The structure by which the plate 12 is fixed to the interior of the enclosure is provided so as to permit the dismantling of the plate 12, as well as its movement between an upper working position in which the catheters 24, like the apparatuses 30 are immersed in the chemical preparation cells 10 corresponding thereto, and a lower maintenance position making it possible to carry out maintenance on said tubes and on said apparatuses.

An embodiment of a support structure permitting the dismantling of the plate 12, as well as its lowering into the lower maintenance position will now be described relative to FIGS. 2 and 3.

The installation of the horizontal support plate 12 within the enclosure is ensured by two vertical pillars 86 located in the vicinity of the rear wall 20c of the enclosure. On its rear edge turned towards the wall 20c, the plate 12 has two rectangular notches 88 for fitting onto the pillars 86. The rear face of each of the pillars 86 normally bears against a horizontally axed roller 90 carried by a lever 92 articulated on the horizontal plate 12 by a horizontal pin 94. More specifically, said horizontal pin 94 is mounted in a part 95 fixed to the plate 12. The lever 92 is normally immobilized by a locking stud 96 in the position illustrated in continuous line form in FIGS. 2 and 3, where the roller 90 is in contact with the rear face of the corresponding pillar 86.

The mechanism which has just been described normally ensures a sliding connection between the plate 12 and the pillars 86 when the locking pins or studs 96 are not retracted.

When it is necessary to dismantle the plate 12, with the aid of grippers an operator retracts the locking studs 96, which frees the levers 92 and allows the rotation thereof by gravity about their pins or spindles 94. The levers 92 then automatically occupy a position illustrated in mixed line form in FIG. 3, in which the rollers 90 are laterally cleared towards the outside with respect to the rear faces of the pillars 86. The plate 12 can then be separated from the pillars 86.

In order to normally immobilize the support plate 12 along the pillars 86 in its upper working position, each of the said pillars has on its front face a horizontal lug 98 on which can be placed a hook 100 articulated on the part 95, about a horizontal axis advantageously constituted by the pivot pin 94 of the lever 92.

Figure 3:
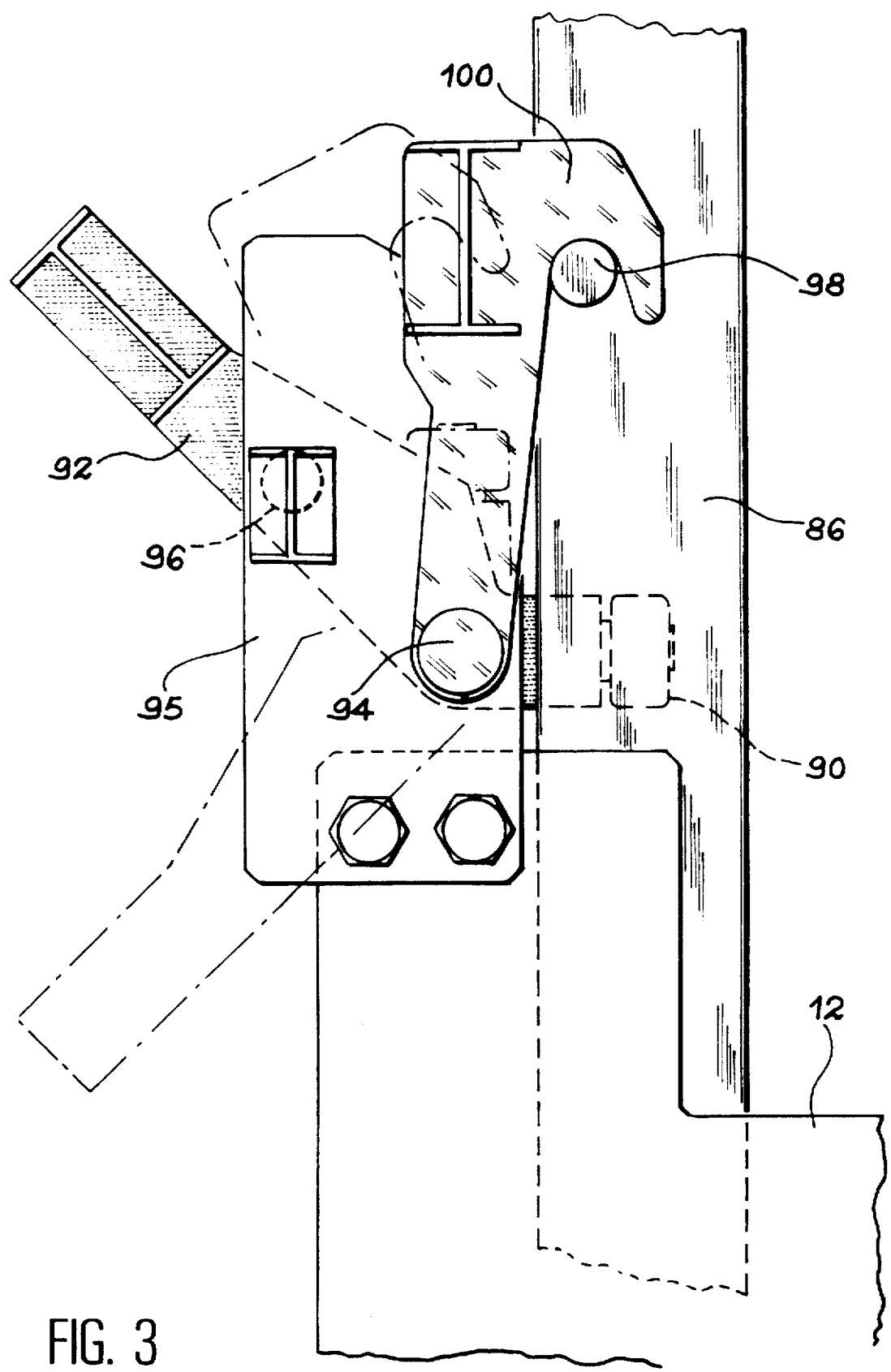
FIG. 3 A side view along arrow F in FIG. 2.

When a maintenance intervention requiring the lowering of the support plate 12 has to take place, the operator raises slightly the plate with the aid of grippers and then tilts towards the outside the hooks 100, into the retracted position illustrated in mixed line form in FIG. 3. The plate 12 can then be lowered into the lower maintenance position, which frees the entire zone in which are located the catheters 24, the apparatuses 30 and the ducts 70, 72.

The exact configuration of the assemblies associated with each of the chemical preparation cells 10 and by which the reagents, the diluting water, the rinsing liquid and the drying air are brought into the cell is dependent on the nature of the analyses to be subsequently carried out in the analysis cell 36 of the corresponding analysis line. The number and nature of the apparatuses 30 optionally supported by these assembles are also dependent on the nature of said analyses.

Figures 4, 5:
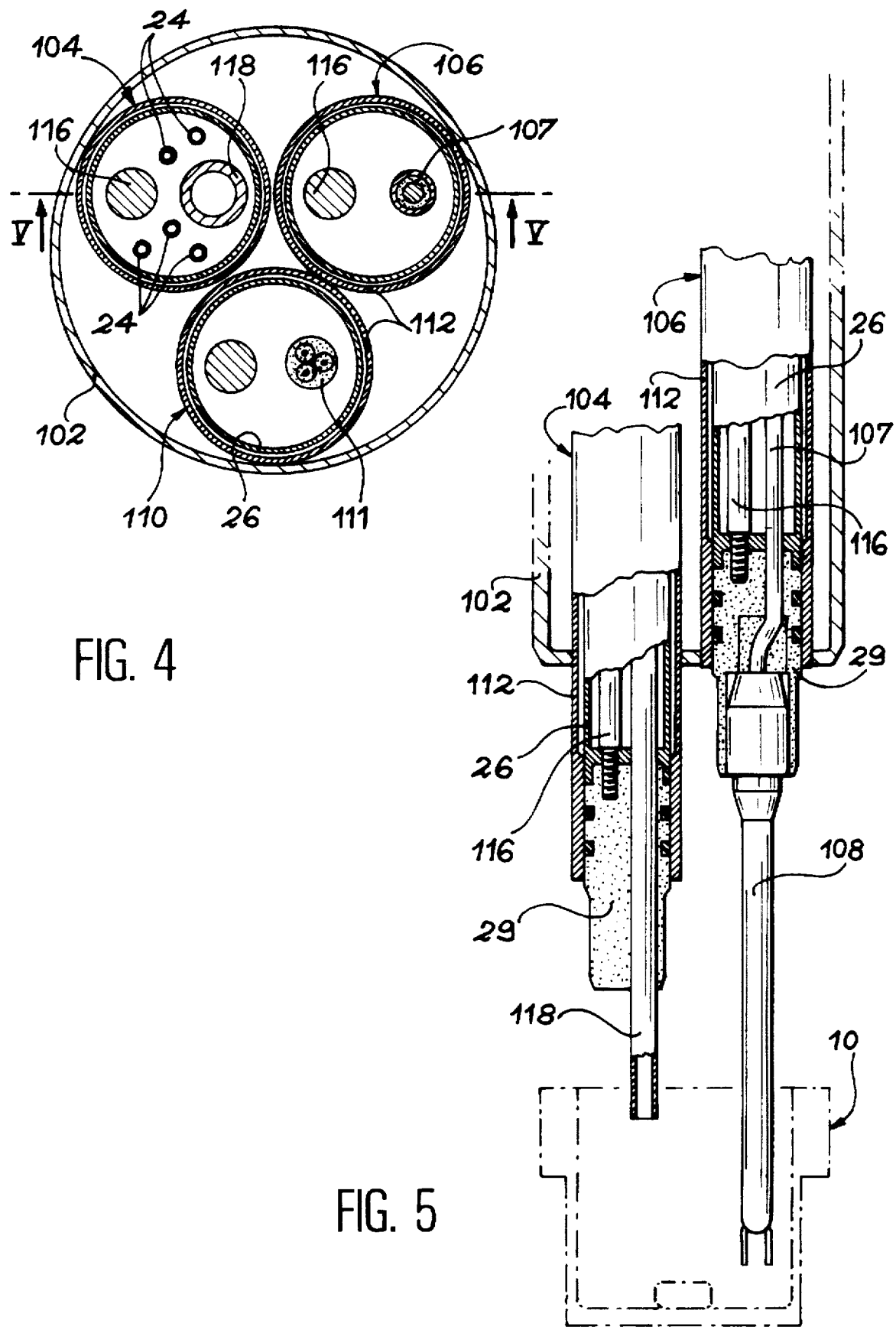
FIG. 4 A sectional view along a horizontal plane of a reagent injection and control assembly equipping one of the analysis lines of the automated analysis apparatus of FIGS. 2 and 3.
FIG. 5 A sectional view along line V—V of FIG. 4.

As illustrated by FIGS. 4 and 5, each of the assemblies has a vertical tubular envelope 102 closed at its ends and which traverses the top flange 20a, whilst being tightly fixed to the latter. The tubular envelope 102 houses one to three subassemblies such as reagent supply assembly 104, a subassembly 106 carrying a conductimetry probe 108 or a subassembly 110 carrying a not shown temperature probe.

Each of these subassemblies 104, 106 and 110 incorporates an external envelope tube 112 in which is tightly received the guide tube 26 of FIG. 1, sealed at its ends by the plugs 28 and 29. These plugs are connected by a vertical rod 116 ensuring the mechanical strength of the corresponding subassembly.

In the case of the reagent supply subassembly 104, one or more capillary tubes 24 pass vertically into the guide tube 26 and through the plugs 28 and 29, in order to connect the reagent injectors 22 (FIG. 1) to the corresponding chemical preparation cell 10. One or more, larger diameter tubes 118 can also pass vertically into the guide tube 26, e.g. in order to ensure the supply of diluting water into the chemical preparation cell 10 in question.

The subassemblies 106 and 110 respectively carrying the conductimetry probe 108 and the temperature probe (not shown) respectively have a vertical coaxial cable 107 and a cable 111 formed from three vertical electric conductors, which connect the corresponding probes to external instrumentation through the enclosure top flange 20a.

Preferably, the external envelope tubes 112 are fixed to the external envelope 102 of the corresponding assembly and the guide tubes are able to slide upwards into the external envelope tubes in order to permit the replacement of the corresponding subassembly, whilst still ensuring a confinement when the different subassemblies are in place.

The control of the automated analysis apparatus illustrated in FIGS. 1 to 5 is brought about in autonomous manner with the aid of the microprocessor 50, which according to previously established programs controls the putting into operation of the motor 16 of the stirrers, the reagent injectors 22, the rinsing and drying means, the air ejectors 44, 62, the analysis apparatuses 37 associated with the analysis cells 36, etc. This control ensures in a satisfactory manner the simultaneous control of several analyses without interferences with the process controller controlling the upstream systems and in particular the distributing means 18.

Figures 6, 7:
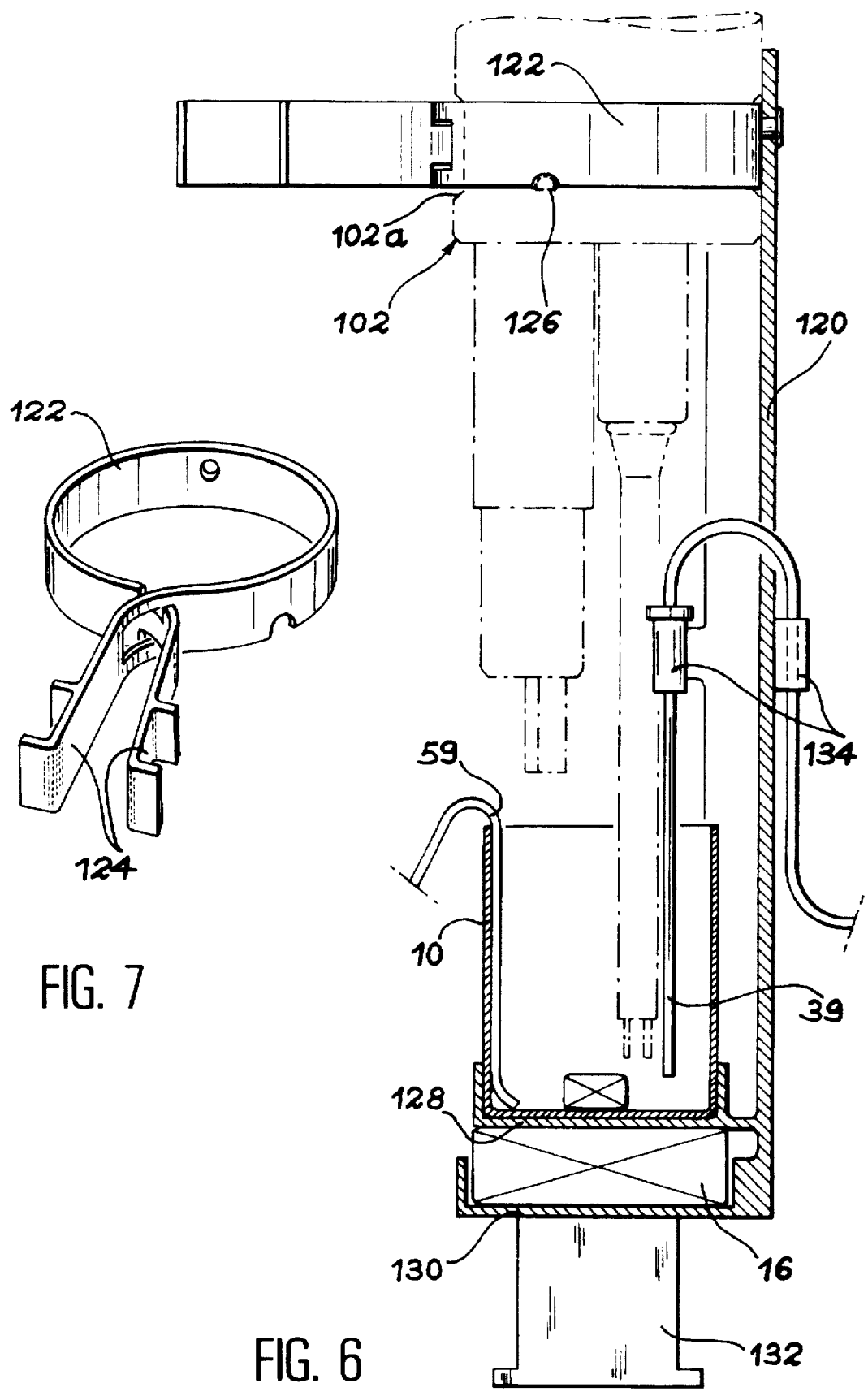
FIG. 6 A side view in part section illustrating a second embodiment of the invention, in which each chemical preparation cell is installed on an individual support.
FIG. 7 A perspective view illustrating a detail of the individual support of FIG. 6.

In a second embodiment of the invention, which will now be briefly described relative to FIGS. 6 and 7, each of the chemical preparation cells 10 is fitted independently of the other cells on an individual support 120, which can be placed on the lower portion of the vertical tubular envelope 102 of the corresponding analysis line. With the aid of a single gripper, this arrangement makes it possible to put into place and maintain each cell 10, whilst ensuring a total independence between the different analysis lines.

More specifically, the individual support 120 is in the form of a vertical post, e.g. having a circular arc-shaped, horizontal section. At its upper end, said vertical post is joined to a fixing collar 122, which can be installed on the lower part of the vertical tubular envelope 102.

The collar 122 is an articulated collar with a rapid and preferably spring-based closure. As is diagrammatically illustrated in FIG. 7, it is equipped with a double gripper 124 making it possible to attach and detach the collar with respect to the envelope 102 with the aid of a single handling gripper. When the collar 122 is released, it penetrates a smaller diameter region 102a of the tubular envelope 102 (FIG. 6). The angular positioning of the support 120 with respect to the vertical axis of the envelope 102 can in particular be ensured by a lug 126 projecting radially to the outside on the smaller diameter region 102a of the envelope and able to penetrate a notch formed in the collar 122.

At its lower end, the support 120 carries a first horizontal plate 128 on which rests the analysis cell 10, as well as a second horizontal plate 130, located beneath the plate 128 and on which is placed the stirrer 16. A gripping member 132 is mounted beneath the second plate 130. The support 120 can also be equipped with guides 134 used for the installation of the rigid tube 39 of the transfer line. The rigid tube 59 of the discharge line is incorporated into the cell 10.

The preceding, non-limitative description of embodiments shows that the automated analysis apparatus according to the invention makes it possible to simultaneously perform several analyses whilst limiting the total duration thereof to the duration of the longest analysis. Therefore there is an improvement to the productivity, at the same time as a significant reduction in the amount of solid waste and liquid effluents.

Moreover, the embodiments described make it possible to easily integrate the apparatus according to the invention into an existing enclosure, without the latter having to undergo major modifications.

It should be noted that the distributing means can be constituted by a system completely different from that described and e.g. incorporating an arm performing a rectilinear translation movement above the chemical preparation cells 10, e.g. by means of a worm or endless screw device, a robot or any other such system. In this case, the cells 10 will be aligned instead of arranged in circular arc manner.

We claim:

1. Automated analysis apparatus for simultaneously performing several analyses on a liquid sample, said automated analysis apparatus comprising:

at least two analysis lines, each including a fixed chemical preparation cell for the liquid sample, means for injecting chemical reagents into said chemical preparation cell, means for stirring liquid in said chemical preparation cell, an analysis cell equipped with analysis means for analyzing the liquid sample, transfer means for transferring liquid in said chemical preparation cell into said analysis cell and from said analysis cell to an effluent discharge system, and discharge means for directly discharging liquid in said chemical preparation cell to said effluent discharge system;

said transfer means including pumping means for pumping liquid, a first tube connecting said chemical preparation cell to said analysis cell and providing a first passage so that liquid can be transferred from said chemical preparation cell to said analysis cell, a second tube connecting said analysis cell to said pumping means and providing a second passage so that liquid can be transferred from said analysis cell to said pumping means, a third tube connecting said pumping means to said effluent discharge system and providing a third passage so that liquid can be transferred from said pumping means to said effluent discharge system, and a valve located in said second tube for selectively opening and closing said second passage;

distributing means for introducing the liquid sample to be analyzed into said chemical preparation cell of each of said analysis lines;

control means for controlling at least the stirring means, the injection means, the analysis means, the transfer means, and the discharge means of each of the analysis lines; and a single fluid-tight enclosure containing said chemical preparation cell of each of said analysis lines and having a top flange, said injection means comprising at least one injection apparatus outside said enclosure and at least one catheter connecting said injection apparatus to said chemical preparation cell, said catheter passing through said top flange and being placed, beneath said flange, in a vertical guide tube.

2. The apparatus according to claim 1, wherein said pumping means is an air ejector common to each of said analysis lines.

3. The apparatus according to claim 2, wherein said air ejector has a programmed delay, constant pressure, motorized air supply.

4. The apparatus according to claim 2, wherein said discharge means includes another air ejector common to each of said analysis circuits, a fourth tube connecting said chemical preparation cell to aid another air ejector and providing a fourth passage so that liquid can be transferred from said chemical preparation cell to said another air ejector, a fifth tube connecting said another air ejector to said effluent discharge system and providing a fifth passage so that liquid can be transferred from said another air ejector to said effluent discharge system, and an another valve located in said fourth tube for selectively opening and closing said fourth passage.

5. The apparatus according to claim 4, wherein said valve and said another valve are each a pneumatic control valve positioned outside the enclosure.

6. The apparatus according to claim 4, wherein said valve and said another valve are each an electrovalve embedded in a protective resin.

7. The apparatus according to claim 1, wherein each of said analysis lines also includes a pipe for supplying rinsing liquid to said chemical preparation cell and a pipe for drying said chemical preparation cell.

8. The apparatus according to claim 1, wherein each of said chemical preparation cells is installed on a first receptacle plate vertically mobile between an upper working position and a lower maintenance position.

9. The apparatus according to claim 1, wherein each of said chemical preparation cells is mounted to an individual support having an articulated collar fixing said individual support to said vertical guide tube.

10. The apparatus according to claim 1, wherein said distributing means comprises a vertical suction fitting installed on means for positioning said suction fitting above a container containing the liquid to be analyzed and above any of said chemical preparation cells.

11. The apparatus according to claim 1, wherein each of said analysis lines also includes one of measuring means and inspection means placed in said chemical preparation cell and a vertical cable connecting the one of said measuring means and said inspection means to an installation outside said enclosure.

* * * * *

UNITED STATES PATENT AND TRADEMARK OFFICE
CERTIFICATE OF CORRECTION

PATENT NO. : 5,776,418
DATED : July 7, 1998
INVENTOR(S) : Besnier et al.

It is certified that error appears in the above-identified patent and that said Letters Patent is hereby corrected as shown below:

On the title page, Section [75] Inventors, delete "Sonnobeaunout-Hague" and insert --Beaumont-Hague--.

On the title page, Section [75] Inventors, delete "Querqueviue" and insert --Querqueville--.

Column 10, line 13, delete "aid" and insert --said--.

Signed and Sealed this

Twenty-fourth Day of November, 1998

Attest:

BRUCE LEHMAN

Attesting Officer

Commissioner of Patents and Trademarks